United States Patent [19]

Clark

[11] Patent Number: 5,106,879

[45] Date of Patent: * Apr. 21, 1992

[54] TREATMENT FOR INFLAMMATORY SKIN DISEASE

[76] Inventor: Lealand L. Clark, 1025 S. 12th East, Salt Lake City, Utah 84102

[*] Notice: The portion of the term of this patent subsequent to Jun. 2, 2004 has been disclaimed.

[21] Appl. No.: 683,511

[22] Filed: Apr. 8, 1991

Related U.S. Application Data

[63] Continuation of Ser. No. 334,816, Apr. 5, 1989, abandoned, which is a continuation of Ser. No. 43,145, Apr. 27, 1987, abandoned, which is a continuation of Ser. No. 692,017, Jan. 15, 1985, Pat. No. 4,670,471, which is a continuation of Ser. No. 482,199, Apr. 5, 1983, abandoned, which is a continuation-in-part of Ser. No. 317,976, Nov. 3, 1981, abandoned.

[51] Int. Cl.$^5$ ............................................. A61K 31/045
[52] U.S. Cl. .................................... 514/724; 514/887
[58] Field of Search ................................ 514/724, 987

[56] References Cited

U.S. PATENT DOCUMENTS 4,670,471 6/1987 Clark .................................... 504/724

Primary Examiner—Leonard Schenkman
Attorney, Agent, or Firm—Mallinckrodt & Mallinckrodt

[57] ABSTRACT

A treatment for inflammatory disorders, such as herpes simplex, eczema, shingles, atopic dermatitis, psoriasis, etc. The treatment includes the topical application of an ointment base containing a small quantity ot triacontanol. The triacontanol-ointment preparation is applied directly to the infected skin area as often as is needed.

9 Claims, No Drawings

TREATMENT FOR INFLAMMATORY SKIN DISEASE

CROSS REFERENCE TO RELATED APPLICATION

This application is a continuation of application Ser. No. 07/334,816, filed Apr. 5, 1989, now abandoned, which was a continuation of application Ser. No. 07/043,145, filed Apr. 27, 1987, now abandoned, which was a continuation of application Ser. No. 06/692,017, filed Jan. 15, 1985 which issued into U.S. Pat. No. 4,670,471, which was a continuation of application Ser. No. 06/482,199, now abandoned, filed Apr. 5, 1983, which was a continuation-in-part of application Ser. No. 06/317,976, filed Nov. 3, 1981, now abandoned.

BACKGROUND OF THE INVENTION

The present invention relates to a method for treating inflammatory skin disease and more particularly to a novel method for treating human skin infected with viral infections such as, for example, Herpesvirus, as well as the treatment of other infections of the skin where inflammation is a problem.

By inflammation is meant the destruction and repair of the tissues in response to irritation, and the means whereby the irritant is removed.

Such a definition places no limits on the amount of the response or the degree or kind of irritation. Because irritation by the normal products of growing and dying cells is related to the process of intercellular communication that occurs physiologically, inflammation merges with the normal behavior of tissues. When minimal it may differ only in degree from the normal physiological process by which tissues control their requirements from their blood supply.

Inflammation is necessary for repair as well as for the removal of irritants. However, repair, as in wound healing, differs only quantitatively from those processes which control the normal growth and contour of the tissues.

Swelling of the tissues is initially due to edema fluid, but in more chronic inflammation white cell infiltration may make a main contribution. The tissues themselves often increase in size. Thus acanthosis and an increase in the papillary vasculature is a usual response of the epidermis and upper dermis to irritation. A papular lesion following an insect bite may show a considerable increase in the bulk of the tissue which may persist after the initial edema has been resolved. Pseudo-epitheliomatous hypertrophy is not unusual in uncontrolled inflammation.

Heat is a usual consequence of increased flow of blood through the skin. In acute lesions the skin may be heated as a direct result of a local increase in metabolic rate. In chronic inflammation neither local metabolism nor blood flow may be increased, and the skin may feel cold. Heat loss cannot be exactly correlated with redness, because areas of fast flow may be on the border of a more congested and slow-flowing system. Thus conduction of heat to the surface of the skin may be considerable over a large, deep arceriovenous fistula while the upper dermis may show all the effects of severe stasis consequent on raised venous pressure.

The sensations that accompany inflammation of the skin include burning, stinging, itching and tenderness, and are thus more varied than in most internal organs. Which of these sensations predominates depends in part on the site, depth, intensity and duration of the inflammatory process. Thus in urticaria stinging may accompany transient superficial lesions, itching is the usual sensation in papular urticaria or in lesions due to histamine release, while pain and tenderness may accompany deeper lesions of long duration, as in delayed pressure urticaria.

Inflammation is a response to any irritation, and the mechanism applies equally to infection, sunburn, abrasions, contact dermatitis or the various patterns or angiitis seen in dermatological practice. Studies of the effects of injury to the skin show early and delayed phases of the inflammatory response, and these are similar whether induced by trauma such as pressure or by ultraviolet irradiation, or any of the factors listed.

It would, be extremely desirable to provide an effective treatment for inflammatory skin diseases. Moreover, it would be desirable to provide an improved treatment for Herpesvirus disorders such as eczema, which is safe, having no known side effects in any body locations. Such treatments are described and claimed herein.

Herpesviruses come in 70 different varieties, but only a few are infectious to humans. The viruses infectious to humans include *Herpesvirus hominis*, which causes herpes simplex; *Herpesvirus varicallae*, which causes varicella (chicken pox) and zoster (shingles); the Epstein-Barr virus, which causes monocleosis; and cytomegalovirus, which causes fetal infections. Herpesviruses are also often responsible for fevers, hepatitis, and pneumonia-like illnesses in children and adults, especially those with lowered resistance. Additionally, eczema is caused by Herpesvirus hominis or Poxvirus officinalis, and perhaps other viruses such as Coxsackievirus.

A. HERPES SIMPLEX

Of all the Herpesviruses, the effects of Herpesvirus hominis are by far the most commonly experienced. Herpesvirus hominis, which is responsible for herpes simplex, has two different forms: Type 1 and Type II. Type 1 causes *Herpes labialis* (oral herpes) in the form of cold sores and unsightly lesions around the lips or nose. Type II causes *Herpes genitalis* (genital herpes) in the form of sores that appear below the waist, primarily in the genital area. The two types vary little with respect to the nature of their behavior and either one can take the other's place. Thus, Type II can cause a cold sore while Type I can also infect the genitals. Nevertheless, Type II is responsible for at least about eighty percent (80%) of genital herpes.

Both types I and II can be transmitted by sexual as well as non-sexual contact; however, genital herpes is generally transmitted through sexual intercourse. A Type I infection of the genitals or a Type II infection of the mouth can occur through oral-genital contact. A cold sore virus may be transmitted when two persons kiss or by means as simple as the use of the same towel to wipe their faces. The eyes can be infected simply by rubbing them after touching an infected area. Thus, there are a variety of ways in which herpes simplex viruses I and II can be transmitted. Moreover, although not the usual case, transmission of the viruses can even occur before the symptoms of herpes simplex appear or before the infected person is aware that he or she has herpes simplex.

The symptoms of herpes simplex infections include the development of a cluster of tiny bumps or blisters, sometimes preceded or accompanied by a fever or swollen lymph glands. The blisters then crust over, and the sores disappear—usually within three weeks after the first symptoms. However, the virus remains in the body for a lifetime, hibernating in such places as the salivary glands, the nerve tissue, and the lymph nodes. After recovery from the first attack, subsequent infections may occur over the next few years, until gradually the frequency of attacks diminishes. Occasionally, however, recurrences may appear over the rest of the individual's life. The reappearance of herpes infections is then often triggered by stress, fatigue, exposure to sun, trauma, fever or menstruation.

Other complications may develop in those who are afflicted with a herpes simplex virus. If a person suffering from herpes simplex touches a sore or blister and then rubs his eyes, he may develop a serious eye infection known as herpes keratitis. Thousands of Americans annually lose their sight because of this disease.

For women, genital herpes simplex carries special risks. To begin with, genital herpes simplex has been linked to cancer of the cervix. Female herpes victims are five to seven times more likely to develop cervical cancer than non-infected females. Genital herpes simplex can also cause serious birth defects. A pregnant woman with an active genital herpes simplex infection faces a fifty percent (50%) chance of passing the disease to her baby as the child passes through the birth canal. About fifty percent (50%) of the newborn infants who develop herpes simplex die of the infection; seventy-five percent (75%) of those who survive suffer from blindness or brain damage. Fortunately, if sores are found close to the time of delivery, the doctor can perform a Caesarean-section to prevent infection of the newborn as it passes through the birth canal.

Most Americans have been exposed to the herpes simplex virus; indeed, eighty percent (80%) of the American population carries the herpes simplex virus, and antibodies against the virus have been found in up to ninety-five percent (95%) of blood samples tested. Although some people never experience symptoms, (possibly because their immune systems repulse the virus so it cannot sustain its attack), about seven out of eight people who come in sexual contact with the herpes simplex virus will contract an infection. It is estimated that from thirty (30) to seventy (70) million Americans suffer occasionally from the most common form of herpes simplex infection, that of coldsores. Moreover, it is estimated that from five (5) to twenty (20) million Americans suffer from genital herpes simplex, and that each year, half a million more Americans join these ranks.

Since there has previously existed no known effective treatment for herpes simplex, the total number of persons inflicted with herpes simplex continues to increase. Scientists have tried and rejected many different treatments for herpes such as vitamin C, zinc, ether, and ice packs. It is evident that in the absence of a treatment for herpes simplex, this relatively new veneral disease could potentially reach epidemic proportions.

B. ECZEMA

Another Herpesvirus disorder which plagues many people is atopic eczema. Eczema occurs in primarily three forms: (1) the infantile form, (2) the adult form, and (3) the localized form.

The infantile form of eczema may first appear soon after birth, often by the fourth month of the infant's life. Infantile eczema is generally mainfested as processes which may be red, dry, slightly scaly, cracked, and excoriated, or sometimes moist and oozing. Infantile eczema is most frequently manifested around the face, scalp, neck, and diaper areas. Older children and young adults generally experience manifestation of the disease in the flexural areas and the cheeks. In fewer than half of the individuals inflicted with infantile eczema, the disease clears up by the age of four; yet even in these individuals, the disease may occur at a later age. The majority of eczema victims still experience occasional flare ups through the young adult years, up until about the age of thirty, at which time the disease usually disappears.

The adult form of eczema is generally manifested in the antecubital and popliteal areas, and in some cases around the hands, feet, and face. The infected skin is generally dry, erythematous, and excoriated with bacterial crusting and redness.

The localized form of eczema, which occurs in diverse individuals, is primarily manifested around the wrists, ankles, hands, feet and ears, as well as the perianal, perivulvar, and scrotal regions.

By far the worst consequence of atopic eczema is the pruritis or itching which is associated with this disease. Those inflicted with atopic eczema often find pruritis to be a life-long companion. Any relief to be had from such intolerable itching is gratifying to say the least. There are many factors which play a role in the occurrence of atopic eczema, such as dietetic and emotional factors. Moreover, seasonal fluctuations are an important factor with atopic eczema generally becoming worse during the winter season.

One of the greatest fears of those who are inflicted with atopic eczema, is that these individuals are generally more susceptible to viral infection, and in particular, to infestation by a herpes simplex virus or a vaccinia virus. Additionally, those suffering from atopic eczema are abnormally susceptible to environmental irritants. Consequently, those inflicted with the disease are often advised to wear clothing which is soft and light; to stay away from heat sources; to take brief baths or showers not exceeding five minutes and using a minimal amount of soap; to avoid primary irritants such as paints, cleansers, solvents, chemical sprays, dusts, and the like; and sometimes to change their residence to a warm, dry temperature, unvarying climate where temperature extremes are rarely experienced.

Although there is no known cure for atopic eczema, there are various helpful treatments which all have one goal in common: to stop the intolerable itching that accompanies atopic eczema. Examples of these treatments include antiseptics, for example antibacteral cleansers such as Betadine (a registered trademark owned by Purdue Frederick Co.; Norwalk, Conn. 06856) and Hibitaine; topical glucocorticoid creams; systemic glucocorticoids; antipruritic agents; and antibiotics. Although the atopic and systemic glucocorticoid treatments have proven most effective in treating long-continued atopic eczema, adverse topical and systemic effects are often experienced when such treatments are used. Consequently, adverse effects in those undergoing glucocorticoid treatments must be carefully monitored.

It is important to the activity of any pharmaceutical agent, that an effective formulation be designed. Effective formulations for many topical agents include creams. Creams are solid emulsions containing suspensions or solutions of medicinal agents for external application. More precisely, preparations of this type come under the classification of ointments, i.e., the emulsion type bases. Other ointment bases are the oleaginous, absorption, and water-soluble bases. See, Remington's Practice of Pharmacy, Eds. E. W. Martin & E. F. Cook, 1956, p. 336. Of these, oleaginous bases "do not yield their medicaments with any degree of certainty", and, accordingly are disfavored. Id. at p. 337, column 2.

The emulsion base called Hydrophilic Ointment, U.S.P. XV differs from oleaginous bases in having an aqueous phase and an emulsifying agent in addition to an oleaginous phase. Consequently, it has a much smaller amount of fatty substance such as petrolatum than an oleaginous base. The smaller amount of "petrolatum does not interfere with the release of medicinal agents." Id. at p. 340. Column 1.

Compositions containing triacontanol for application to the skin are disclosed by Gebhart et al. U.S. Pat. No. 3,584,115. Gebhart et al. disclosed compositions containing propellant gases, such as the freons, and employed long chain alcohols such as triacontanol as a marker that would turn white upon application to a surface such as the skin. Gebhart et al. also disclosed the addition of medicinal agents such as medicinal ointments such as oleaginous ointment bases. There, the medicinal agent was itself the oleaginous ointment and not anything carried with it. As mentioned, the prior art teaches that oleaginous ointments make unreliable carriers. Gebhart et al. neither discloses nor suggests a composition wherein triacontanol is a medicinal agent in a composition that delivers it in a pharmaceutically effective manner to the skin.

BRIEF SUMMARY OF THE INVENTION

The present invention is based upon the discovery that triacontanol has been found to be an effective agent for treating inflammatory skin diseases infected with viral infections such as Herpesvirus or other skin diseases such as dermatitis (eczema), contact dermatitis, seborrheic dermatitis, atopic dermatitis, scaling papular diseases such as psoriasis and the like. The invention will be described in greater detail in conjunction with the treatment of Herpesvirus infections such as herpes simplex infections and atopic eczema but as will appear more fully hereinafter the present invention is not limited to these skin diseases as other skin diseases where inflammation is a problem have been successfully treated with triacontanol.

DETAILED DESCRIPTION OF THE INVENTION

The novel anti-inflammatory of the present invention, triacontanol, is preferably used in association with a pharmaceutically acceptable carrier, such as a hydrophilic ointment, designed to be applied topically to human skin infected with viral infections or other skin diseases where inflammation is a problem.

Thus the present invention relates to a method for treating inflammatory skin disease. Each of the treatments for the various types of dermatitis is substantially the same, and includes the topical application of a preparation comprising a suitable pharmaceutically acceptable carrier containing a small amount of triacontanol. The triacontanol preparation may be applied periodically to an infected skin area as needed. Indeed, clinical experiments indicate that the preparation may be applied several times daily without identifiable side effects. Consequently, the preparation may be applied whenever needed to alleviate discomfort or to clear up lesions. Shortly after application of the preparation to a dermatitis the pain and itching associated with it disappears. Repeated application causes the dermatitis to disappear, often within a few days.

The active ingredient in the preparation is triacontanol. Triacontanol, also known as melissyl alcohol, myricyl alcohol, or hydroxy-triacontane, is a straight-chain, aliphatic, thirty carbon waxy alcohol having the formula $CH_3(CH_2)_{28}CH_2OH$. Although triacontanol has been found useful for such purposes as the fertilization of crops, to the inventor's knowledge, triacontanol has not been used as the active ingredient in any medical treatment.

Experimental application of triacontanol to skin infected with a Herpesvirus shows that triacontanol has the following advantageous qualities: (1) it removes pain and itching; (2) it clears up lesions associated with Herpesviruses such as herpes simplex lesions; (3) it is anti-inflammatory; (4) it restores lipid levels on the skin to normal levels (important with respect to dermatitis such as eczema); (5) it is virus and bacteria static; and (6) it is safe and has no known side effects in any body locations.

The triacontanol preparation is prepared by simply mixing a very small quantity of triacontanol, about one hundredth of one percent (0.01%) by weight, with a medicant base until thoroughly blended. Although 0.01% triacontanol has been found sufficient for effective treatment, quantities much smaller than this are also likely to provide effective treatment. Generally from about 0.01% to about 1% with 0.1% being preferred may be used.

An important consideration in the preparation is the choice of an appropriate medicant base. The selected medicant base must be compatible with the triacontanol so as to maintain it in active form for effective application. One ointment which has been employed in the present invention is a standard USP hydrophilic ointment; a thousand grams of which contains the following compounds in the indicated amounts:

| Hydrophilic Ointment - USP | |
| --- | --- |
| Compound | Amount |
| Methylparaben | 0.25 g. |
| Propylparaben | 0.15 g. |
| Sodium lauryl sulfate | 10 g. |
| Propylene glycol | 120 g. |
| Stearyl alcohol | 250 g. |
| White petrolatum | 250 g. |
| Purified water | 370 g. |

The ingredients of hydrophilic ointment USP, which ointment is commonly available from a variety of commercial sources, are combined as follows. First, the stearyl alcohol and the white petrolatum are melted on a steam bath and warmed to about 75° C. The other ingredients are dissolved in the purified water and are also warmed to about 75° C. All ingredients are then mixed together and stirred until the mixture congeals.

It will be understood that the hydrophilic ointment disclosed above is given by way of example only, and that numerous other carrier medicants may also be suitable, such as an oleic acid ointment base. Again, it is the triacontanol, not the carrier medicant, which is the active ingredient in the preparation, the carrier medicant merely acting as a carrier for the triacontanol to provide for the effective application of the triacontanol in active form to the skin. Thus, it will be appreciated that one of the most important properties of the carrier medicant is its ability to provide sufficient contact between the active triacontanol and the skin to effectively treat the skin.

The above-described triacontanol-hydrophilic ointment preparation has been found to be effective in the treatment of viral disorders such as dermatitis caused by simplex, eczema, and zoster (shingles). The preparation has also been found useful in the treatment of other skin diseases such as seborrheic dermatitis, contact dermatitis, atopic dermatitis and psoriasis. Moreover, the triacontanol-hydrophilic ointment preparation has been found to be effective against acne and perioral dermatitis [as outlined in my related copending application, Serial No. 318,076, filed Nov. 3, 1981, which is incorporated herein by reference].

Experimentally, the best results have been obtained in using the preparation in the treatment of herpes simplex (all types of lesions, particularly cold sores) and eczema. Although the effect of the triacontanol preparation on other Herpesvirus disorders such as chicken pox, mononucleosis, fetal infections, fevers, hepatitis, and pneumonia-like illnesses is yet unknown, it is well-anticipated that the preparation may also be effective in the treatment of these disorders.

Over thirty patients with herpes simplex lesions in the form of cold sores have been treated with the above-described triacontanol-hydrophilic ointment preparation. Upon topical application of the preparation, these patients typically found that the itching associated with the herpes simplex lesions disappeared after about 30 to 60 seconds and that the pain also disappeared after about four to eight minutes. The effectiveness of the preparation in aiding the healing process was found to vary with the age of the lesion. Typically, it was found that if a lesion was treated within four hours after its initial appearance, the lesion disappeared completely within only a few hours—commonly within about six hours. For older lesions, it was found that treatment caused the lesions to disappear in about one to seven days, generally reducing the normal life of the lesion by at least fifty percent (50%). Overall, the triacontanol-hydrophilic ointment preparation decreased the normal healing time for herpes simplex lesions by up to eighty percent (80%) or more.

Analysis of the data from thirty subjects indicated that they had herpes simplex for variable lengths of time, from one to 45 years, with a mean of 12 years. In this group, herpes reoccured one to 18 times per year with a mean of six times per year.

Triacontanol significantly reduced healing time in the 27 cases where healing time was indicated pre- and post-treatment (pr. 0.0001). The mean healing time for previous lesions was 10.9 days with a range from 3 to 21 days. The mean healing time after treatment with triacontanol was 4.4 days with a range of 1 to 14 days.

Twenty-six out of twenty-eight (93%) subjects indicated that triacontanol decreased healing time. When further asked to quantify how much triacontanol decreased healing time, the mean response was an 80% decrease.

Forty patients with atopic ezcema were also treated with the above-described triacontanol-hydrophilic ointment preparation. The average patient treated had experienced the symptoms of atopic eczema for at least ten years and had suffered from the symptoms of atopic eczema during at least forty percent (40%) of the previous year. These patients found that their eczema lesions, which were four weeks old on the average, were completely healed five days after beginning treatment with the triacontanol ointment preparation. This is in contrast to the three week healing period which is generally required when the well-known cortisone cream treatments were used.

Moreover, the severe itching associated with the eczema lesions disappeared within two hours after application of the triacontanol-hydophilic ointment preparation, whereas the cortisone creams required about two weeks to dispell the itching. Additionally, the pain and soreness associated with the lesions commonly disappeared within only a few minutes after application of the triacontanol-hydophilic ointment preparation, as opposed to about five days for the cortisone creams. Finally, the triacontanol-hydrophilic ointment preparation decreased the normal healing time for the lesions dramatically.

As shown below treatment for various types of disorders caused by skin inflammation and most importantly, an anti-inflammatory treatment for the following diseases as set forth in Tables 1–3 has been successfully used.

| Viral Disorders responsive to triacontanol | Patients |
| --- | --- |
| Herpes Simplex | 30 |
| Shingles | 5 |

TABLE 2

| Disorders generally responsive to triacontanol | Patients |
| --- | --- |
| Seborrheic dermatitis | 34 |
| Eczema | 40 |
| Lichen Simplex Chronicus | 8 |
| Pruritus ani | 3 |
| Psoriasis | 12 |
| Later phase of contact dermatitis | 12 |
| Later phase of irritant dermatitis | 20 |
| Xerosis | 22 |

TABLE 3

| Disorders less responsive to triacontanol | Patients |
| --- | --- |
| Lichen planus | 2 |
| Dermatitis herpetiformis | 1 |
| Lichen sclerosis et atrophicans | 1 |

One of the significant advantages of using triacontanol as the active ingredient in the treatment of the present invention is that triacontanol has proven itself to be safe. Indeed, it occurs naturally in alfalfa, honey, and in the waxy portions of several edible plants. Recently, it was found that triacontanol dramatically increases crop yields when used as a fertilizer. A group at Michigan State University discovered that when as little as five milligrams of triacontanol were mixed with 30 to 40 gallons of water in the treatment of one acre of crops, growth was increased by an average of 12 percent. Since triacontanol is a common plant constituent, it is not unusual for one to consume enough triacontanol in one meal to treat at least an acre of crops.

Another indication that triacontanol is safe is the fact that it is found naturally in beeswax as a palmitate ester and possibly, in extremely small amounts, as the simple alcohol itself. Beeswax has been used for many years as a stiffening agent in many pharmaceutical preparations such as cerates, ointments, pastes, and petroxolins. Cerates are mostly used as dressings for inflamed skin surfaces and contain sufficient beeswax to give them a desired consistency. Moreover, many cosmetic preparations such as all-purpose creams, night creams, vanishing creams, lotions, mascaras, lipsticks, cream lip rouge, and face and body makeup contain significant amounts of beeswax. Thus, the long-time use of beeswax-containing preparations may provide a basis for the belief that triacontanol is safe when applied topically.

Although found in many preparations presently on the market, it is unclear why, if any triacontanol is present in beeswax as the free alcohol, it is not active against herpes simplex and other Herpesvirus disorders. First of all, since it is present in beeswax as the palmitate, it is thought that triacontanol is not active when in the form of a palmitate ester. Moreover, it is conjectured that even if a very small amount of triacontanol is present as a free alcohol in beeswax, perhaps the amount is too small to be effective or perhaps the environment imposed by the other constituents of beeswax in some way prohibits the triacontanol from having any effect. This supposed inhibitive effect could be due in part to hydrophobic interaction between triacontanol molecules in the beeswax environment. Additionally, the inactivity of any triacontanol in beeswax might also possibly be explained by the inability of the skin to effectively absorb any triacontanol from the beeswax environment. Furthermore, it is also possible that very close contact between the triacontanol and the monomolecular cell wall of the virus is required for effective treatment. Such close contact could very well be inhibited by the beeswax environment surrounding any triacontanol which might be present. Whatever the reason for the ineffectiveness of beeswax in treating Herpesvirus disorders, for purposes of the present invention, it will be appreciated that the choice of an appropriate carrier medicant for the triacontanol such as the hydrophilic ointment described hereinabove, is very important.

It will be appreciated that the invention may be embodied in other specific forms without departing from its spirit or essential characteristics. The foregoing descriptions are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United State Letters Patent is:

1. A method for treating inflammatory skin diseases which comprises applying to said skin in need of such treatment an effective amount of triacontanol as a medically active ingredient in a compatible carrier being devoid of propellant gases.

2. A method according to claim 1 in which the triacontanol is present in an amount from about 0.01% to about 1.0% by weight.

3. A method according to claim 1 in which the carrier is a hydrophilic ointment.

4. A method according to claim 1 in which the carrier is an oleic acid based carrier.

5. A composition for the treatment of inflammatory skin disease comprising triacontanol as a medically active ingredient; and a compatible carrier ointment base devoid of propellant gases suitable for topical application to the skin of a user and effective to provide sufficient contact between the triacontanol and the skin to effectively treat the skin.

6. A composition for the treatment of inflammatory skin disease according to claim 5, wherein the carrier ointment base is a hydrophilic ointment.

7. A composition for the treatment of inflammatory skin disease according to claim 6, wherein the tricontanol is present in the range from about 0.01% to about 1.0% by weight of the composition.

8. A composition for the treatment of inflammatory skin disease according to claim 5, wherein the carrier is an oleic acid based carrier.

9. A composition for the treatment of inflammatory skin disease according to claim 8, wherein the triacontanol is present in the range from about 0.01% to about 1.0% by weight of the composition.

* * * * *